(12) United States Patent
Kosturko et al.

(10) Patent No.: US 9,782,109 B2
(45) Date of Patent: Oct. 10, 2017

(54) APPARATUS FOR MEASURING THE LUMINANCE AND TEMPERATURE OF A LIGHT SOURCE OF A SPECTROPHOTOMETRIC DEVICE

(75) Inventors: William Kosturko, Milford, CT (US); John K. Gamelin, Avon, CT (US)

(73) Assignee: CAS Medical Systems, Inc., Branford, CT (US)

( * ) Notice: Subject to any disclaimer, the term of this patent is extended or adjusted under 35 U.S.C. 154(b) by 680 days.

(21) Appl. No.: 13/543,180

(22) Filed: Jul. 6, 2012

(65) Prior Publication Data
US 2013/0012822 A1    Jan. 10, 2013

Related U.S. Application Data

(60) Provisional application No. 61/504,927, filed on Jul. 6, 2011.

(51) Int. Cl.
*A61B 5/1455*    (2006.01)

(52) U.S. Cl.
CPC .... *A61B 5/1455* (2013.01); *A61B 2560/0252* (2013.01); *A61B 2562/0238* (2013.01); *A61B 2562/0271* (2013.01)

(58) Field of Classification Search
CPC .............. A61B 5/1455; A61B 5/14551; A61B 5/14552; A61B 5/0002; A61B 5/0059; A61B 5/14532; A61B 5/72
USPC ....... 600/309, 310, 322, 323, 331, 340, 344, 600/473, 474; 356/41
See application file for complete search history.

(56) References Cited

U.S. PATENT DOCUMENTS

| | | |
|---|---|---|
| 5,477,853 A | 12/1995 | Farkas et al. |
| 5,715,173 A | 2/1998 | Nakajima et al. |
| 6,723,054 B1 * | 4/2004 | Baruch et al. ................ 600/342 |
| 2009/0182209 A1 | 7/2009 | Benni |
| 2009/0259407 A1 | 10/2009 | Gerlitz |
| 2009/0292186 A1 * | 11/2009 | Xu ..................... A61B 5/14532 600/316 |

OTHER PUBLICATIONS

EP Search Report for EP 12175451.9 dated Oct. 22, 2012.

* cited by examiner

*Primary Examiner* — Eric Winakur
*Assistant Examiner* — Chu Chuan (JJ) Liu
(74) *Attorney, Agent, or Firm* — O'Shea Getz P.C.

(57) ABSTRACT

A system for measuring the luminance and temperature of a light source element of a spectrophotometric device is provided. The system includes a photodiode, a luminance measuring device, a temperature measuring device, a first switch, and a controller. The photodiode is operable to receive light signals emitted by the light source element and passing through a subject's body tissue. The luminance measuring device is operable to measure luminance of the light signals received by the photodiode. The temperature measuring device is operable to measure the temperature of the photodiode. The first switch is operable to connect the photodiode to the luminance measuring device or the temperature measuring device. The controller is operable to control the connection of the first switch.

6 Claims, 5 Drawing Sheets

APPARATUS FOR MEASURING THE LUMINANCE AND TEMPERATURE OF A LIGHT SOURCE OF A SPECTROPHOTOMETRIC DEVICE

Applicant hereby claims priority benefits under 35 U.S.C. §119(e) of U.S. Provisional Patent Application No. 61/504,927 filed Jul. 6, 2011, the disclosure of which is herein incorporated by reference.

BACKGROUND OF THE INVENTION

Spectrophotometric devices are used to non-invasively measure biological tissue oxygenation by subjecting tissue to various wavelengths of light and observing tissue absorption characteristics. Light-emitting diodes (LEDs) are frequently used as the light source in these spectrophotometric devices because they are small, inexpensive, and available at a variety of wavelengths. LEDs can be problematic, however, because their output characteristics, such as luminous intensity and center wavelength, can change based on factors like drive current, temperature, and aging. In particular, temperature can be highly variable, especially when the spectrophotometric device is used in conjunction with techniques such as therapeutic hypothermia. As a result, the above-mentioned factors (i.e., drive current, temperature, etc.) require precise measurement or control to maintain accuracy of the spectrophotometric device. In one known control mechanism, the spectrophotometric device controls drive current to the LEDs to maintain a consistent light output from the part. This control mechanism only provides an indirect indicator of the actual light produced by the LEDs and does not monitor changes due to temperature variations.

In U.S. Pat. No. 5,477,853, Farkas and Lewis disclose methods for monitoring LED output characteristics using measurements of the forward voltage generated across the LED at various drive currents. Farkas and Lewis disclose that deviations from reference voltages were correlated with several output characteristics of the LED, including luminous intensity, temperature, and hence wavelength. As these output characteristics are based on a single measurement value (i.e., LED forward voltage), the measurements are not unique and are subject to error with increasing deviations from nominal values. It is therefore desirable to decouple the measurements and to use more direct means for monitoring the output characteristics.

What is needed, therefore, is a system for measuring the luminous intensity and temperature of a light source of a spectrophotometric device, which system decouples luminous intensity and temperature measurements and uses direct means for monitoring both output characteristics.

SUMMARY OF INVENTION

According to an aspect of the present invention, a system for measuring the luminance and temperature of a light source element of a spectrophotometric device is provided. The system includes a photodiode, a luminance measuring device, a temperature measuring device, a first switch, and a controller. The photodiode is operable to receive light signals emitted by the light source element and passing through a subject's body tissue. The luminance measuring device is operable to measure luminance of the light signals received by the photodiode. The temperature measuring device is operable to measure the temperature of the photodiode. The first switch is operable to connect the photodiode to the luminance measuring device or the temperature measuring device. The controller is operable to control the connection of the first switch.

According to another aspect of the present invention, a NIRS sensor is provided. The NIRS sensor includes an LED light source and a photodiode. The photodiode is operable to receive light signals emitted by the light source element and passing through a subject's body tissue. The photodiode is disposed within sufficient proximity of the light source so as to enable measurement of the luminance and temperature of the light source. The photodiode is adapted to send signals to one or both of a luminance measuring device operable to measure luminance of the light signals received by the photodiode, and a temperature measuring device operable to measure the temperature of the photodiode.

These and other objects, features and advantages of the present invention will become apparent in light of the detailed description of the invention provided below, and as illustrated in the accompanying drawings.

DETAILED DESCRIPTION OF THE INVENTION

Figure 1:
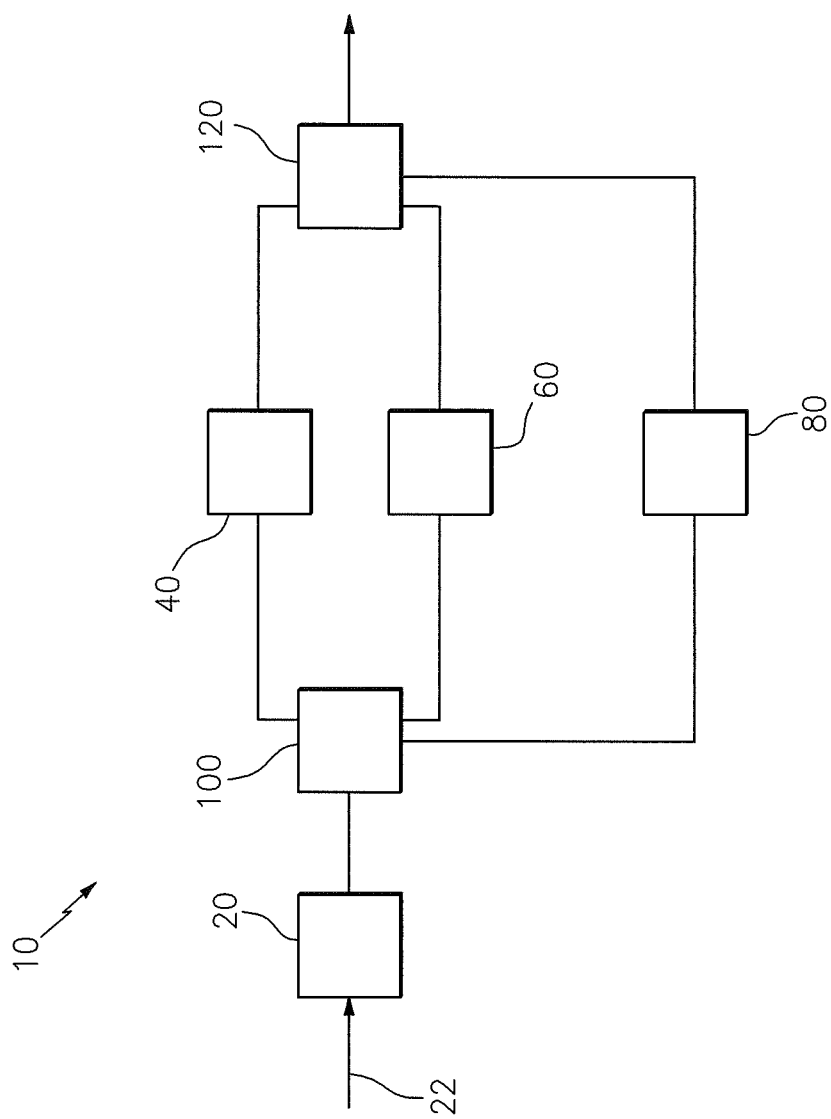
FIG. 1 is a block diagram of a system for measuring the luminance and temperature of a light source of a spectrophotometric device.

Referring to FIG. 1, a block diagram of a system 10 for measuring the luminous intensity (i.e., luminance) and temperature of a light source of a spectrophotometric device is illustrated. The system 10 includes a photodiode 20, a luminance measuring device 40, a temperature measuring device 60, a controller 80, a first switch 100 and a second switch 120. The photodiode 20 is operable to receive light signals 22 emitted by a light source of a spectrophotometric device and passing through a subject's body tissue. The luminance measuring device 40 is operable to measure luminance of the light signals 22 received by the photodiode 20. The temperature measuring device 60 is operable to measure the temperature of the photodiode 20. The first switch 100 is operable to connect the photodiode 20 to the luminance measuring device 40 or the temperature measuring device 60. The second switch 120 is operable to connect the spectrophotometric device to the luminance measuring device 40 or the temperature measuring device 60. The controller 80 is operable to control the connection of the first and second switches 100, 120.

Figure 2:
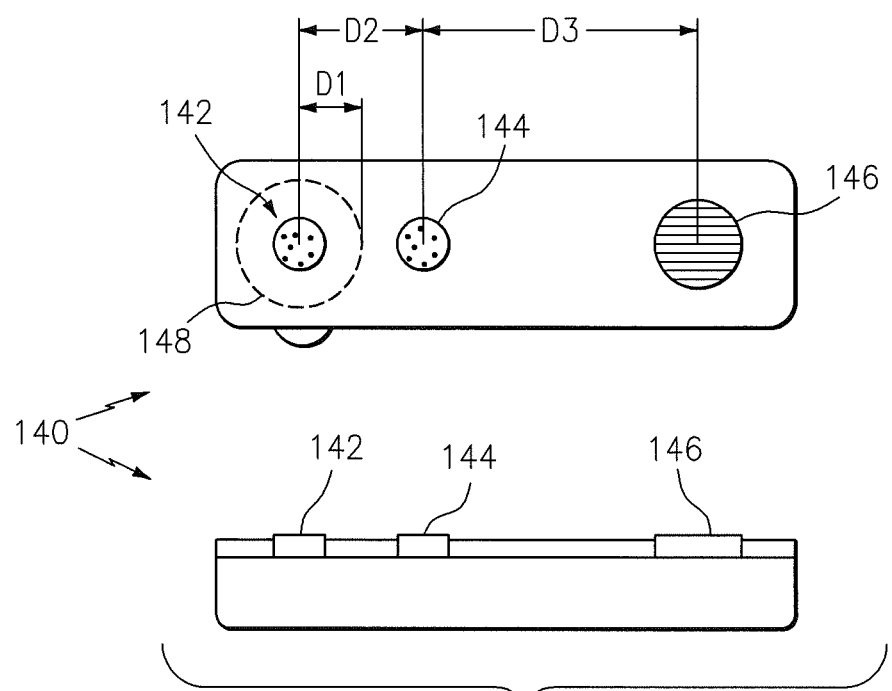
FIG. 2 is a diagrammatic illustration of the NIRS device disclosed in U.S. patent Publication Ser. No. 12/090,671.

An example of an acceptable spectrophotometric device includes the near-infrared spectroscopy (NIRS) device disclosed in U.S. patent Publication Ser. No. 12/090,671 (hereinafter "the '671 application"), which is hereby incorporated by reference in its entirety. Briefly stated, the NIRS device includes a NIRS sensor 140 and a processor. The NIRS sensor 140, illustrated in FIG. 2, includes a light source 142, a near light detector 144 and a far light detector 146. The NIRS sensor 140 is adapted for use with the processor, which provides signals to and/or receives signals from the NIRS sensor 140. The light source 142 is selectively operable to emit infrared light. The light source 142 may comprise, for example, a LED or a laser diode. A light guide (e.g., fiber optics) may be used to guide light emitted by the light source 142 from the sensor 140 to the testing site (i.e., the subject's skin). The near light detector 144 and the far light detector 146 each include a light responsive transducer such as a photodiode that is operative to sense luminous intensity derived from light emitted by the light source 142 after such light passes through the subject's body. The light detectors 144, 146 are electrically connected to the processor of the NIRS device. The relative spacing between the light source 142, near light detector 144 and far light detector 146 is of considerable importance relative to the sensing desired. In a preferred embodiment, the relative spacing includes: (1) a separation distance ("D2") between the light source 142 and the near light detector 144 that is great enough such that the near light detector 144 is positioned outside of any optical shunt field 148 (the shunt field 148 extends a distance "D1" out from the light source 142); and (2) the separation distance ("D3") between the far light detector 146 and the near light detector 144 is greater than the separation distance between the light source 142 and the near light detector 144 (i.e., D3>D2>D1). The present system 10 is not limited to use with the NIRS device described in the '671 application. In alternative embodiments, the NIRS sensor 140 may include one or more of the luminance measuring device 40, temperature measuring device 60, first switch 100, second switch 120, and controller 80.

The photodiode 20 of the present system may comprise any commercially available photodiode. In embodiments in which one of the near light detector 144 and the far light detector 146 of the NIRS sensor 140 is a photodiode, the near light detector 144 or the far light detector 146 may function as the photodiode 20 of the present system 10. In other embodiments, the photodiode 20 of the present system 10 may be a separate element from the near light detector 144 and the far light detector 146 of the NIRS sensor 10. For ease of description, the photodiode 20 of the present system 10 will be described hereinafter as being a separate element from the near light detector 144 and the far light detector 146 of the NIRS sensor 140.

Figure 3:
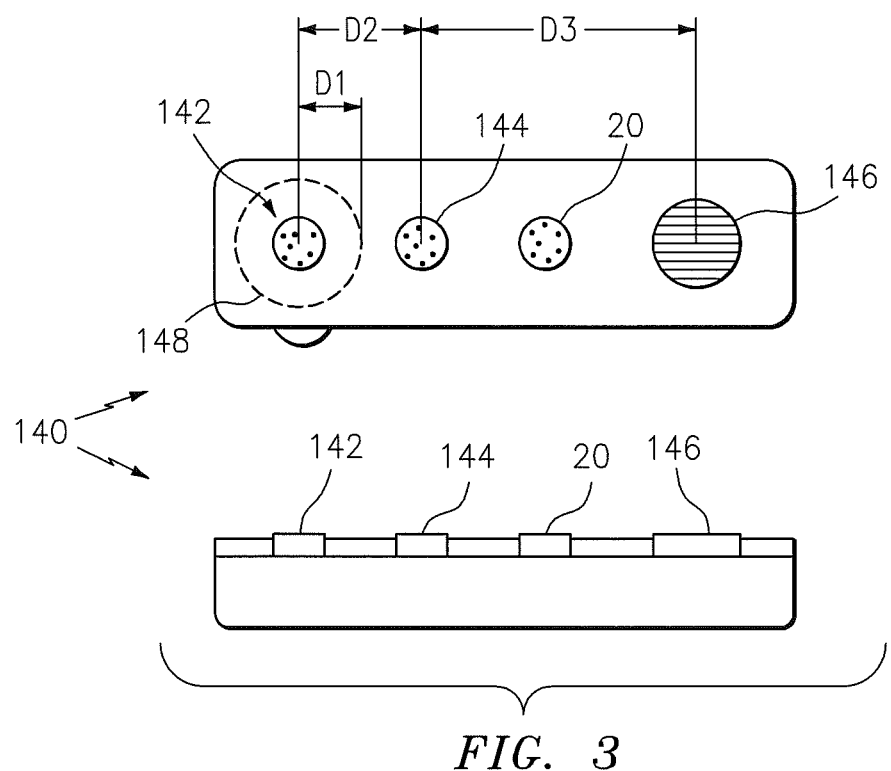
FIG. 3 is a diagrammatic illustration of a NIRS sensor with the photodiode of the present system disposed therein.

Referring to FIG. 3, the photodiode 20 is disposed within the package of the NIRS sensor 140. The photodiode 20 is disposed within sufficient proximity of the light source 142 of the NIRS sensor 140 so as to enable measurement of the luminance and temperature of the light source 142. An example of an acceptable photodiode is a silicon-based photodiode. The present system 10 is limited to use with any particular photodiode, however.

Figure 4:
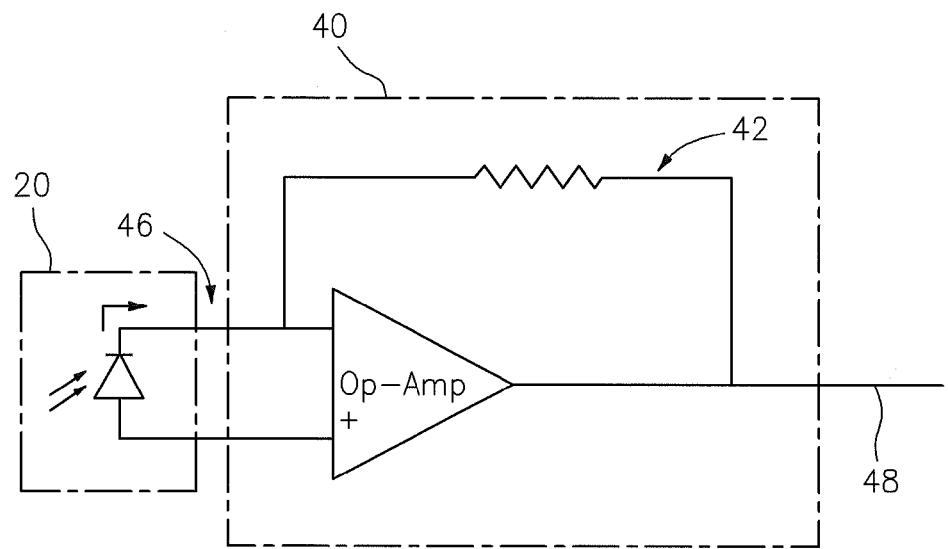
FIG. 4 is a circuit diagram showing a luminance measuring device.
Figure 5:
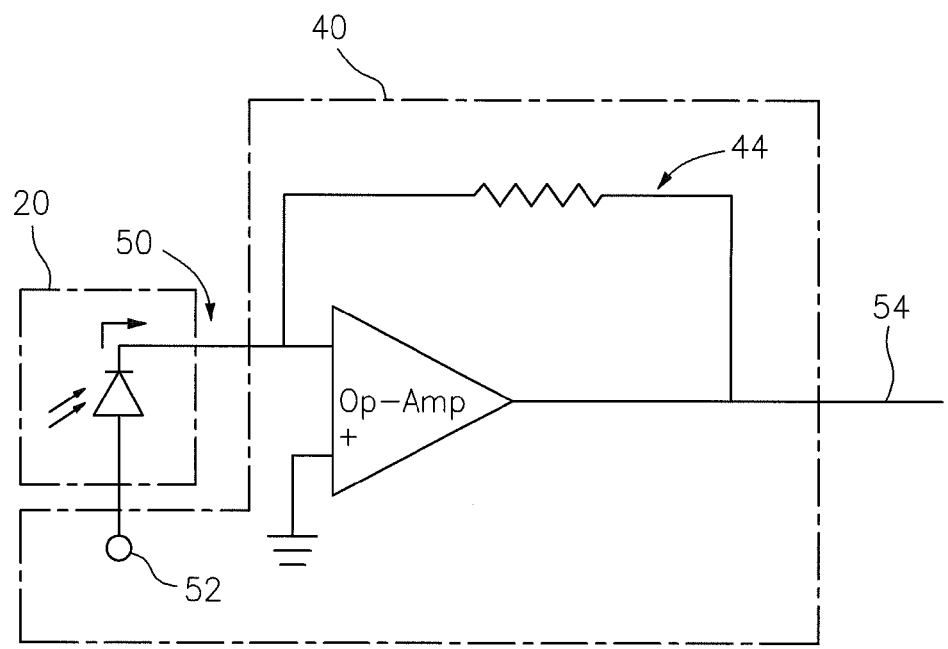
FIG. 5 is a circuit diagram showing a luminance measuring device.

Referring now to FIGS. 4 and 5, the luminance measuring device 40 comprises circuitry 42, 44 for converting a signal received from the photodiode 20 into a signal indicative of the luminance of the light signals received by the photodiode 20. In one embodiment, illustrated in FIG. 4, the luminance measuring device 40 comprises a photovoltaic circuit 42. FIG. 4 illustrates the configuration that results after the controller 80 controls the first switch 100 to connect the photodiode 20 to the luminance measuring device 40, as is described further below. The input 46 of the photovoltaic circuit 42 receives signals from the photodiode 20. The photovoltaic circuit 42 is zero biased and has a zero ohm input impedance. The output 48 of the photovoltaic circuit 42 is connected to the second switch 120 (see FIG. 1). The photovoltaic circuit 42 is well-suited for applications in which accuracy of the luminance measurements is emphasized relative to the speed of the measurements. In another embodiment, illustrated in FIG. 5, the luminance measuring device 40 may comprise a photoconductive circuit 44. FIG. 5 illustrates the configuration that results after the controller 80 connects the photodiode 20 to the luminance measuring device 40, as is described further below. The input 50 of the photoconductive circuit 44 receives a signal from the photodiode 20. The photoconductive circuit 44 has a reverse voltage bias 52 applied. The output 54 of the photoconductive circuit 44 is connected to the second switch 120 (see FIG. 1). The photoconductive circuit 44 is well-suited for applications in which the speed of the luminance measurements is emphasized relative to the accuracy of the measurements. The luminance measuring device 40 is not limited to any particular photoconductive circuit embodiment.

Figure 6:
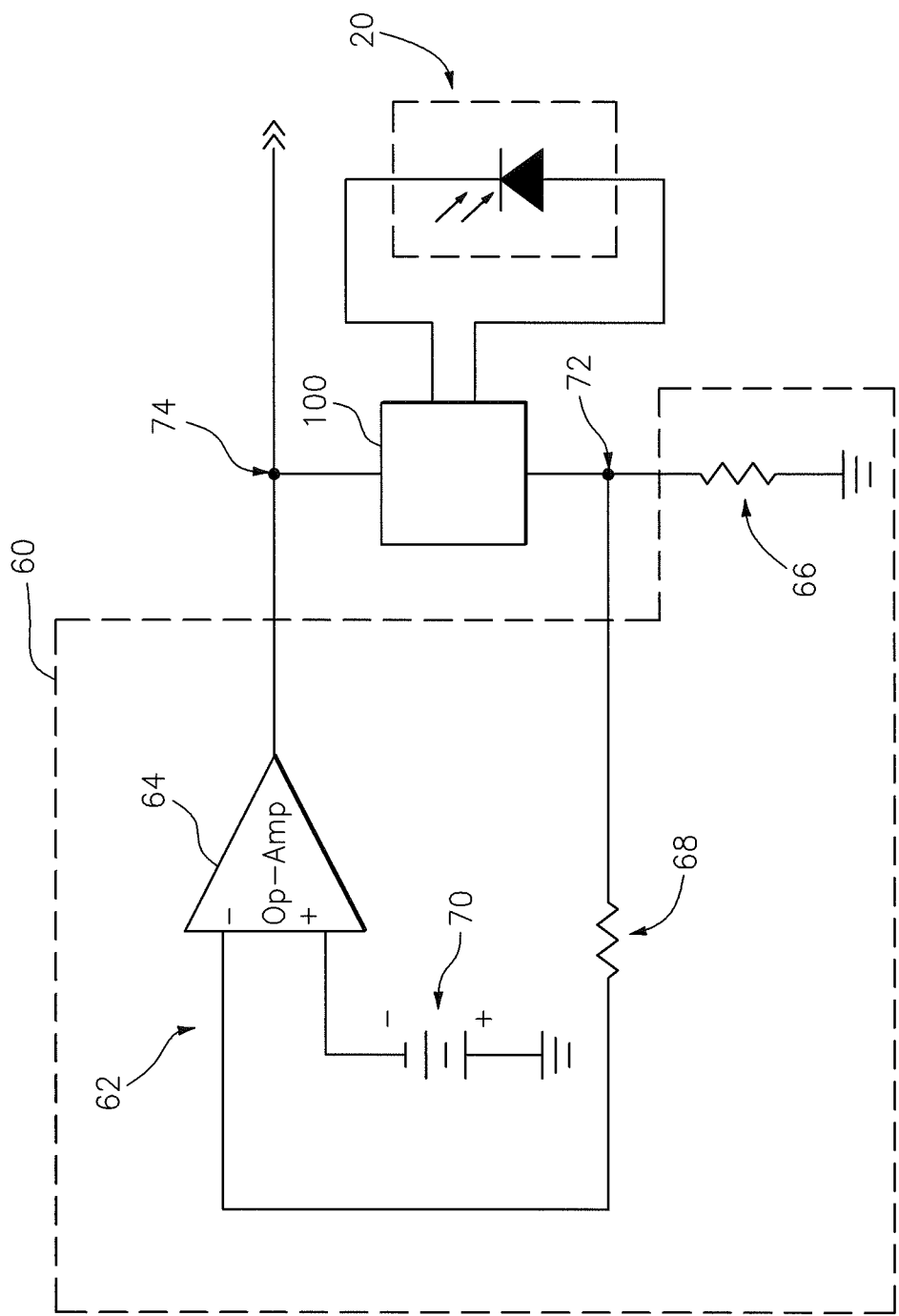
FIG. 6 is a circuit diagram showing a temperature measuring device.

Referring now to FIG. 6, the temperature measuring device 60 comprises a circuit 62 for converting a signal received from the photodiode 20 into a signal indicative of the temperature of the photodiode 20. In the preferred embodiment, illustrated in FIG. 6, the temperature measuring device 60 comprises a circuit 62 that biases the photodiode 20 with a constant current. The circuit 62 comprises an op-amp 64, a first load 66, a second load 68 and a voltage source 70. The input 72 of the circuit 62 receives a signal from the photodiode 20. The output 74 of the circuit 62 is connected to the second switch 120 (see FIG. 1). This embodiment utilizes the temperature sensitivity inherent in all silicon photodiodes; e.g., the voltage across a silicon photodiode biased with constant current will decrease approximately 2 millivolts (2 mV) for every 1 degree Celsius (IC) increase in temperature. The temperature measuring device 60 may further comprise a unity gain differential amplifier (not shown) operable to adjust the output 74 to account for the nominal voltage of the photodiode 20. The temperature measuring device 60 may further comprise an amplifier (not shown) for adding gain to the output 74. The magnitude of the gain may vary depending on the resolution required by the spectrophotometric device. While the temperature measuring device 60 is described in terms of its preferred embodiment, it is not limited to any particular embodiment.

Referring again to FIG. 1, the first switch 100 is disposed between the photodiode 20, the luminance measuring device 40 and the temperature measuring device 60. The first switch 100 is operable to connect the photodiode 20 to one of the luminance measuring device 40 or the temperature measuring device 60. The first switch 100 is operable to receive electronic signals from, and is operable to be controlled by, the controller 80. In the preferred embodiment, the first switch 100 comprises a semiconductor CMOS analog switch. The first switch 100 is not limited to this embodiment, however.

Referring again to FIG. 1, the second switch 120 is disposed between the luminance measuring device 40 and the temperature measuring device 60 and the spectrophotometric device. The second switch 120 is operable to connect one of the luminance measuring device 40 or the temperature measuring device 60 to the spectrophotometric device (i.e., the processor of the NIRS device). The second switch 120 is operable to receive electronic signals from, and is operable to be controlled by, the controller 80. In the preferred embodiment, the second switch 120 comprises a semiconductor CMOS analog switch. The second switch 120 is not limited to this embodiment, however.

Referring again to FIG. 1, the controller 80 is operable to control the connections of the first switch 100 and the second switch 120. That is, with regard to the first switch 100, the controller 80 is operable to control whether the first switch 100 connects the photodiode 20 to the luminance measuring device 40 or to the temperature measuring device 60. Similarly, with regard to the second switch 120, the controller 80 is operable to control whether the second switch 120 connects the luminance measuring device 40 or the temperature measuring device 60 to the spectrophotometric device. The controller 80 is preferably adapted for providing signals to and/or receiving signals from the spectrophotometric device (i.e., the processor of the NIRS device).

Operation

During operation of the NIRS device, the present system 10 selectively alternates between luminous intensity measurement and temperature measurements of the photodiode 20. The configuration (i.e., connection) of the first and second switches 100, 120 determines whether luminous intensity or temperature is being measured. The controller 80 simultaneously controls the configuration of the first and second switches 100, 120 such that when the first switch 100 connects the photodiode 20 to the luminance measuring device 40, the second switch 120 connects the luminance measuring device 40 to the spectrophotometric device (i.e., the processor of the NIRS device), and such that when the first switch 100 connects the photodiode 20 to the temperature measuring device 60, the second switch 120 connects the temperature measuring device 60 to the spectrophotometric device (i.e., the processor of the NIRS device). The outputs 48, 54, 74 of the luminance measuring device 40 and temperature measuring device 60 provide signals to the processor of the NIRS device, and the processor is operable to adjust the intensity of the light source 142 in response thereto. The processor may make adjustments based on information relating to light sensitivity characteristics or temperature characteristics that were recorded at time of manufacture into a memory device permanently associated with the processor.

Although this invention has been shown and described with respect to the detailed embodiments thereof, it will be understood by those skilled in the art that various changes in form and detail thereof may be made without departing from the spirit and the scope of the invention.

What is claimed is:

1. A system for measuring the luminance and temperature of a light source element of a spectrophotometric device, the system comprising:

a photodiode configured to receive light signals emitted by the light source element and passing through a subject's body tissue, and to produce first signals;

a luminance measuring device configured to measure luminance of the light signals received by the photodiode, using the first signals from the photodiode;

a temperature measuring device configured to measure the temperature of the photodiode, using the first signals from the photodiode;

a first switch configured to create a first communication path for the first signals to travel from the photodiode to the luminance measuring device or a second communication path for the first signals to travel from the photodiode to the temperature measuring device;

a controller configured to control the first switch to create the first communication path for the first signals to travel from the photodiode to the luminance measuring device or the second communication path for the first signals to travel from the photodiode to the temperature measuring device.

2. The system of claim 1, further comprising:

a second switch configured to create a third communication path between the spectrophotometric device and the luminance measuring device or a fourth communication path between the spectrophotometric device and the temperature measuring device;

wherein the controller is further configured to control the second switch to create the third communication path between the spectrophotometric device and the luminance measuring device or the fourth communication path between the spectrophotometric device and the temperature measuring device.

3. The system of claim 2, wherein the controller is configured to simultaneously control the first and second switches.

4. The system of claim 1, wherein the luminance measuring device comprises a photovoltaic circuit.

5. The system of claim 1, wherein the luminance measuring device comprises a photoconductive circuit.

6. The system of claim 1, wherein the temperature measuring device comprises a circuit configured to simulate a constant current source.

* * * * *